Figure 1:
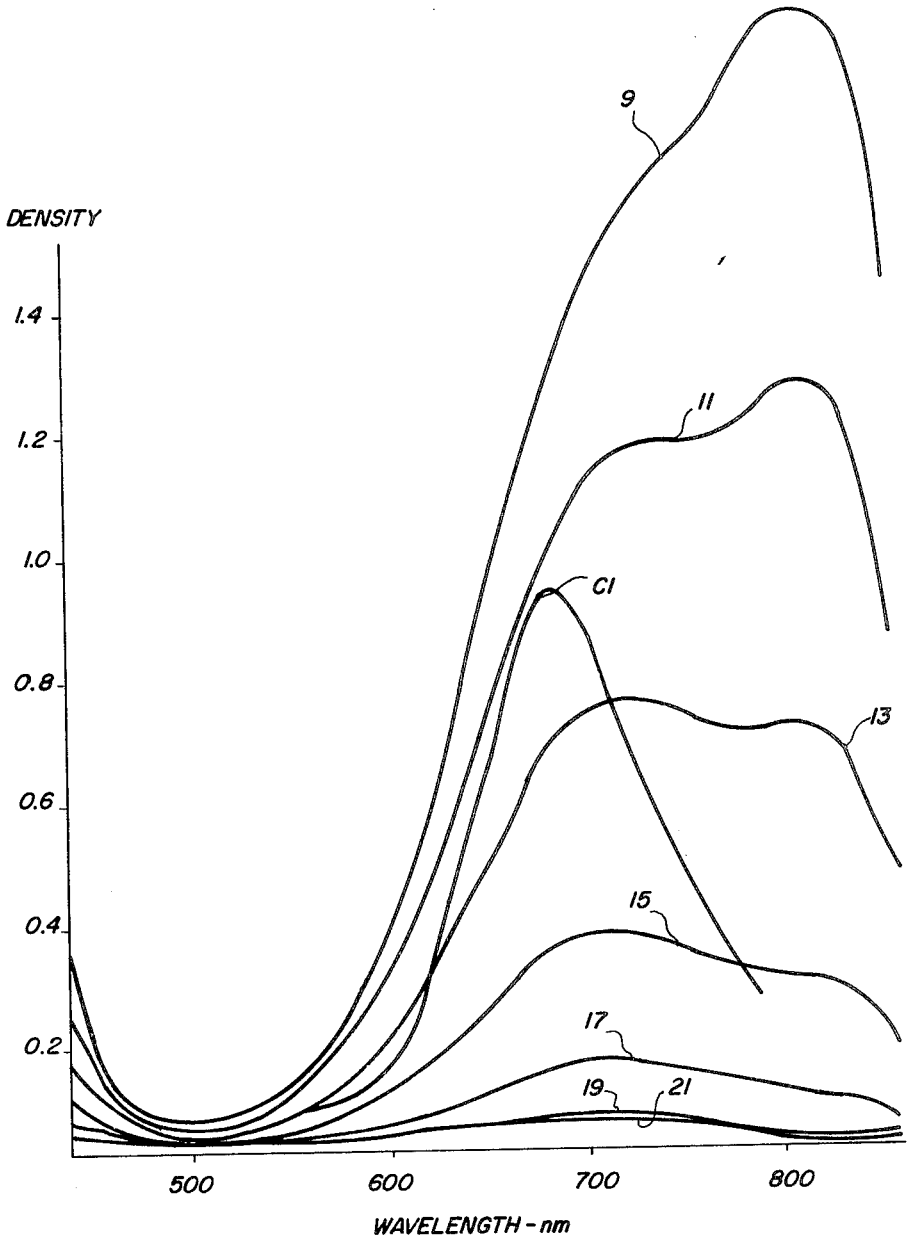

United States Defensive Publication [19] (H) [11] T990,004

Fernandez et al. [43] Jan. 1, 1980

[54] FLUORINATED 1-HYDROXY-2-NAPHTHAMIDE COUPLER, COUPLER COMPOSITIONS AND PHOTOGRAPHIC ELEMENTS SUITED TO FORMING INTEGRAL SOUND TRACKS

[76] Inventors: Jose M. Fernandez; Robert G. Cameron; Edward J. Walsh, all c/o Kodak Park Division, Rochester, N.Y. 14650

[21] Appl. No.: 36,261

[22] Filed: May 4, 1979

Related U.S. Application Data

[62] Division of Ser. No. 928,756, Jul. 27, 1978.

[51] Int. Cl.[2] ..... C07C 103/75

[52] U.S. Cl. ..... 260/559 R; 430/533

[57] ABSTRACT

5,6,7,8 Tetrafluoro 1-hydroxy-2-naphthamide couplers which are N-substituted with a lower alkylphenoxybutyl ballasting group are disclosed as well as compositions and photographic elements containing these couplers in coupler solvent particles. The coupler solvent particles are comprised of a combination of a coupler solvent and the coupler capable of permitting the formation of a microcrystalline dye. Surprisingly these microcrystalline dyes exhibit a broadened absorption characteristic in the 750 to 850 nm region of the spectrum. Dye images having such absorption characteristics are particularly suited to forming integral infrared absorbing sound tracks in photographic elements, such as motion picture projection films.

3 Claims, 1 Sheet Drawing,

32 Pages Specification

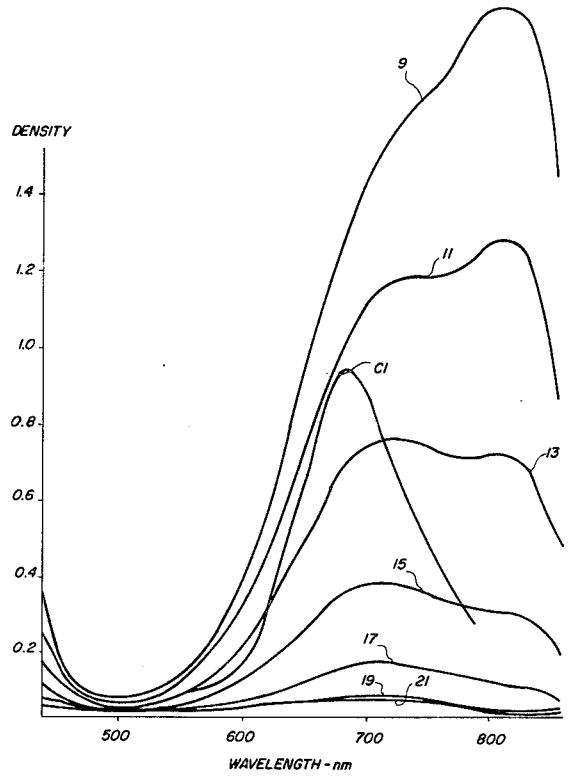

The file of this unexamined application may be inspected and copies thereof may be purchased (849 O.G. 1221, Apr. 9, 1968).